US008709764B2

(12) United States Patent
Possemiers et al.

(10) Patent No.: US 8,709,764 B2
(45) Date of Patent: Apr. 29, 2014

(54) ENZYMATIC DEMETHYLATION OF FLAVONOIDS

(75) Inventors: Sam Possemiers, Ghent (BE); Willy Verstraete, Wondelgem (BE); Arne Heyerick, Gentbrugge (BE); Denis De Keukeleire, Melle (BE)

(73) Assignee: Universiteit Gent, Ghent (BE)

( * ) Notice: Subject to any disclaimer, the term of this patent is extended or adjusted under 35 U.S.C. 154(b) by 1242 days.

(21) Appl. No.: 11/909,709

(22) PCT Filed: Mar. 27, 2006

(86) PCT No.: PCT/BE2006/000024
§ 371 (c)(1),
(2), (4) Date: Jan. 8, 2008

(87) PCT Pub. No.: WO2006/099699
PCT Pub. Date: Sep. 28, 2006

(65) Prior Publication Data
US 2009/0130724 A1   May 21, 2009

Related U.S. Application Data

(60) Provisional application No. 60/665,109, filed on Mar. 25, 2005.

(51) Int. Cl.
*C12P 17/06* (2006.01)

(52) U.S. Cl.
USPC ........................................ 435/125; 435/252.1

(58) Field of Classification Search
None
See application file for complete search history.

(56) References Cited

FOREIGN PATENT DOCUMENTS

JP            61-166355 A      7/1986
WO    WO 2004/089359 A1    10/2004

OTHER PUBLICATIONS

Mahmoud, Dissertation, (http://webdoc.sub.gwdg.de/diss/2005/mahmoud/mahmoud.pdf), 2004, accessed Nov. 5, 2010, pp. 1-390.*
Sakamoto et al.,.International Journal of Food Microbiology 89 (2003) 105-124.*
Heilig et al. (Applied and Environmental Microbiology, Jan. 2002, p. 114-123 vol. 68, No. 1).*
Possemiers et al., "Activation of proestrogens from hops (*Humulus lupulus* L.) by intestinal microbiota: Conversion of isoxanthohumol into 8-prenylnaringenin," *Journal of Agricultural and Food Chemistry* 53: 6281-6288 (2005).
Wang et al., "Human intestinal bacteria capable of transforming secoisolariciresinol diglucoside to mammalian lignans, enterodiol and enterolactone," *Chemical and Pharmaceutical Bulletin* 48: 1606-1610 (2000).
Kreft et al., "Specificity of O-demethylation in extracts of the homoacetogenic *Holophaga foetida* and demethylation kinetics mea-
sured by a coupled photometric assay," *Archives of Microbiology* 167: 363-368 (1997).
Hur and Rafii, "Biotransformation of the isoflavonoids biochanin A, formononetin, and glycitein by *Eubacterium limosum*," *FEMS Microbiology Letters* 192: 21-25 (2000).
Hänsel and Schulz, "Demethylxanthohumol: Isolation from hops and cyclization to flavanones desmethylxanthohumol (Isolierung aus hopfen and cyclisierung zu flavanonen)," *Archiv Der Pharmazie* 321: 37-40 (1988). (English abstract).
Nikolic et al., "Metabolism of xanthohumol and isoxanthohumol, prenylated flavonoids from hops (*Humulus lupulus* L.), by human liver microsomes," *Journal of Mass Spectrometry* 40: 289-299 (2005).
Decroos et al., "Isolation and characterisation of an equol-producing mixed microbial culture from a human faecal sample and its activity under gastrointestinal conditions," *Archives of Microbiology* 183: 45-55 (2005).
Rowland et al., "Bioavailability of phyto-oestrogens," *British Journal of Nutrition* 89: S45-S58 (2003).
Turner et al., "Bioactive isoflavones in functional foods: the importance of gut microflora on bioavailability," *Nutrition Reviews* 61: 204-213 (2003).
International Search Report (PCT/BE2006/000024), mailed Aug. 22, 2006.
Written Opinion of the International Searching Authority (PCT/BE2006/000024), mailed Aug. 22, 2006.
International Preliminary Report on Patentability (PCT/BE2006/000024), mailed Apr. 30, 2007.
Official Action for Russian Patent Application No. 2007139511/13, dated Jul. 1, 2010. English translation provided.
Examiner's First Report on Australian Patent Application No. 2006227572, dated Aug. 31, 2010.
Official Notice for Russian Patent Application No. 2007139511/13, dated Feb. 26, 2010. English translation provided.
Official Action for Chinese Patent Application No. 200680009379.6, dated Nov. 30, 2010.
English translation of Official Action for Chinese Patent Application No. 20068009379.6, dated Nov. 30, 2010.
Official Action for Russian Patent Application No. 2007139511/10, dated Apr. 7, 2011.
English translation of Official Action for Russian Patent Application No. 2007139511/10, dated Apr. 7, 2011.
Hur and Rafii, "Biotransformation of the Isoflavonoids Biochanin A, Formonentin, and Glycitein by *Eubacterium limosum*," *FEMS Microbiol. Letts.* 192:21-25 (2000).
Wang et al., "Human Intestinal Bacteria Capable of Transforming Secoisolariciresinal Diglucoside to Mammalian Lignans, Enterodiol and Enterolactone," *Chem. Pharm. Bull.* 48:1606-1610 (2000).
Official Communication issued in Canadian Patent Application No. 2,602,707, dated Jul. 16, 2012 (4 pages).
Official Action for Russian Patent Application No. 2007139511/13, dated Dec. 8, 2010. English translation provided.
Office Action for Chinese Patent Application No. 200680009379.6, dispatched Jun. 27, 2011.
English Translation of Office Action for Chinese Patent Application No. 200680009379.6, dispatched Jun. 27, 2011.
Office Action for Chinese Patent Application No. 200680009379.6, dated Nov. 2, 2011 (with Translation).

(Continued)

*Primary Examiner* — Irene Marx
(74) *Attorney, Agent, or Firm* — Clark & Elbing LLP

(57) ABSTRACT

The invention discloses the demethylation of 5-methoxyflavonoids by bacterial enzymes, the use of these enzymes in the production of phytoestrogens in vitro, and in pharmaceutical compositions in combination with a source of methylated 5-methoxyprenylflavonoids.

2 Claims, 5 Drawing Sheets

(56) References Cited

OTHER PUBLICATIONS

Figure 1:
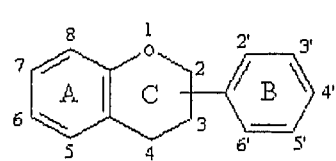
Figure 1:
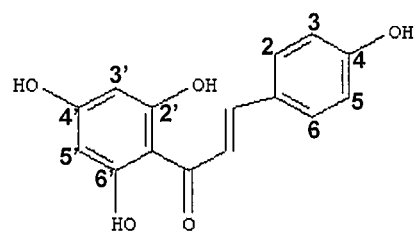
Figure 1:
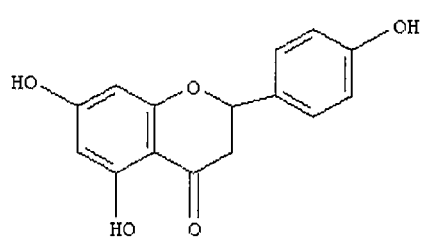
Figure 1:
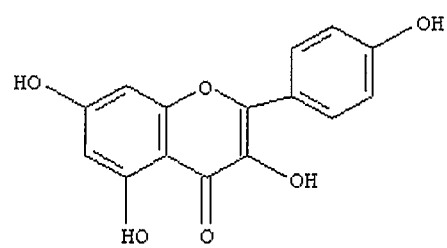
Figure 1:
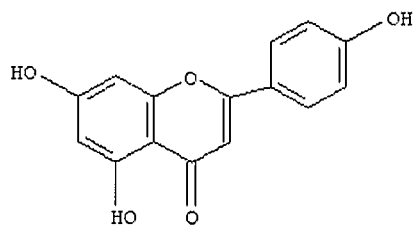
Figure 1:
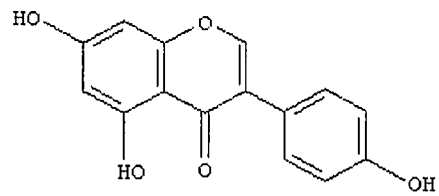

Office Action for Japanese Patent Application No. 502195/2008, dated Oct. 25, 2011 (with Translation).

Hur, Hor-Gil et al. "Biotransformation of the isoflavanoids biochanin A, formononetin, and glycitein by *Eubacterium limosum*" *FEMS Microbiology Letters*, 192:21-25 (2000).

Nikolic, Dejan et al. "Metabolism of Xanthohumol and Isoxanthohumol, Prenylated Flavonoids from Hops (*Humulus lupulus* L.), by Human Liver Microsomes" *J. Mass Spectrom.*, 40:289-299 (2005).

Wang, Li-Quan et al. "Human Intestinal Bacteria Capable of Transforming Secoisolariciresinol Diglucoside to Mammalian Lignans, Enterodiol and Enterolactone" *Chem. Pharm. Bull.*, 48(11):1606-1610 (2000).

Wang, Rong-Fu et al. "PCR Detection and Quantitation of Predominant Anaerobic Bacteria in Human and Animal Fecal Samples" *Applied and Environmental Microbiology*, 62(4):1242-1247 (1996).

Wang, Yongqiang et al. "A Facile Synthetic Approach to Prenylated Flavanones: First Total Syntheses of (±)-Bonannione A and (±)-Sophoraflavanone A" *J. Nat. Prod.*, 64:196-199 (2001).

* cited by examiner

A Flavonoid

B Chalcone

C Flavanone

D Flavonol

E Flavone

F isoflavonoids

ENZYMATIC DEMETHYLATION OF FLAVONOIDS

CROSS-REFERENCE TO RELATED APPLICATIONS

This application is the U.S. National Stage of International Application No. PCT/BE2006/000024, filed Mar. 27, 2006, which claims the benefit of U.S. Application No. 60/665,109, filed Mar. 25, 2005.

FIELD OF THE INVENTION

The present invention relates to phytoestrogens and their preparation as well as to pharmaceutical compounds and food supplements which include such phytoestrogens.

BACKGROUND

Hops (*Humulus lupulus* L.) have been used for centuries as an essential raw material in beer-brewing, providing bitterness and flavor to beer. In the last few years, the plant has gained increasing attention as a source of prenylflavonoids, a flavonoid subclass containing an apolar prenyl-side chain attached to one of the phenolic rings. These are present in the lupulin glands, found at the base of the bracteoles in the hop cones of the female plant. Of these prenylflavonoids two chalcones (xanthohumol (X) and desmethylxanthohumol (DMX)) and three flavanones (isoxanthohumol (IX), 8-prenylnaringenin (8-PN) and 6-prenylnaringenin (6-PN)) (FIG. 2), now receive much attention because of their potential health-promoting properties. X has been identified as a strong cancer chemopreventive agent, while 8-PN has been shown to be one of the most potent phytoestrogens identified so far, with considerably higher activity than the well-known soy phytoestrogens. 8-PN has been demonstrated to display in vivo estrogenic activity, to prevent bone loss in rats, to inhibit angiogenesis and metastasis and has been shown to exhibit anti-androgenic activity.

X is present as a predominant prenylchalcone in the female hop cones in concentrations up to 1% (w/w), whereas DMX is present in lower concentrations (De Keukeleire et al. (2003) *J. of Agric. and Food Chem.* 51, 4436-4441). The X/DMX ratio differs between the hop varieties. By isomerisation, X is transformed into IX and DMX is converted into 8-PN and 6-PN.

The estrogenic effects of hops have been recognized for decades. Hop baths have been used for the treatment of gynecological disorders and menstrual disturbances among female hoppickers were reportedly common. In 1999, Milligan et al. [*J. Clin. Endocrinol. Metab.* 84, 2249-2252], identified a novel phytoestrogen in hop, 8-prenylnaringenin. Although it is much weaker than 17β-estradiol (<1%), it is one of the most potent phytoestrogens identified so far, with a considerably higher activity than other phytoestrogens such as the soy-derived compounds genistein and daidzein.

It is being questioned whether dietary and/or environmental exposure to phytoestrogens could impose health risks such as endocrine disruption. In case of hop prenylflavonoids, beer is the main dietary source. The average beer consumption in the United States was calculated at about 225 ml of beer per capita per day in 2001 (USDA, 2003). When assumed that this amount was consumed as US major brand lager/pilsner beers (500-1000 μg prenylflavonoids/l beer), the daily intake of prenylflavonoids would be about 0.14 mg. However, the concentrations detected in beer (and therefore average intake) strongly depend on the brewing process, as strong ales contain up to 4 mg prenylflavonoids/l. Although X is the predominant prenylflavonoid present in hop (0.1-1% of dry weight), most of it is transformed into IX by thermal isomerisation during worth boiling. Therefore IX is the major prenylflavonoid found in beer and is present in concentrations from 500 μg/l (lager/pilsner) up to 4 mg/l (strong ale). Similarly, DMX is converted into 8-PN resulting in final concentrations in beer of up to 100 μg 8-PN/L. But despite the high activity of 8-PN, the total estrogenic activity in beer is still 500 to 1000 times lower than the concentration needed for harmful in-vivo activity (~100 mg/l) (Milligan et al. (2002) *Reproduction* 123, 235-242). Moreover, many beers are now made using hop extracts instead of whole hops, giving lower concentrations of 8-PN or no 8-PN at all. Therefore, it is generally agreed that based on current knowledge, no detrimental health effects can be attributed to phytoestrogens upon moderate beer consumption.

On the other hand, many data now correlate intentional phytoestrogen intake with possible health benefits (Magee & Rowland (2004) *Br. J. Nutr.* 91, 513-531). Besides beer, hop based dietary supplements are marketed, claiming effects as breast enhancement and reduction of hot flushes. Overall health effects of phytoestrogens potentially result from the action of a combination of many individual phytochemicals with multiple and perhaps additive or interfering activities. Up to now, only isoflavones and lignans are considered relevant phytoestrogens in the human diet, especially because 8-PN concentrations in beer are considered to be too low for positive or negative health effects.

Several patent publications describe beneficial health effects of dietary flavonoids, for example the use of IX to prevent bone density lowering (WO04089359), the use of hop extracts in medicaments having estrogenic properties (WO02085393), and the use of IX or X in food products claiming anti-inflammatory or anti-aging properties (patent WO03090555). Moreover, the use of 8-PN in cosmetics for skin treatment (CA2426467) has also been suggested.

In order to exert in-vivo effects claimed in vitro, dietary flavonoids need to be absorbed from the gut and reach their targets unchanged. In general, monomeric flavonoids pass unmodified through the stomach into the small intestine, where absorption from the gut in the mesenteric circulation can take place. In-vitro studies indicated extensive liver biotransformation of X (Yilmazer et al. (2001a) *FEBS Lett.* 491, 252-256) and 8-PN (Nikolic et al. (2004) *Drug Metabolism and Disposition* 32, 272-279) upon absorption. However, the extent of dietary polyphenol absorption in the small intestine is rather limited (10-20%), thereby implying that a large proportion of the flavonoids reaches the colon. Naringenin, a non-prenylated analogue of 8-PN, showed intensive microbial biotransformation in the intestine, including ring cleavage and dehydroxylation (Rechner et al. (2004) *Free Radic. Biol. Med.* 36, 212-225), followed by absorption and urinary excretion. Little is known about intestinal transformations of prenylflavonoids. Nookandeh et al. (2004) *Phytochemistry* 65, 561-570, dosed 1000 mg/kg body weight of X to rats and isolated 22 metabolites from the feces. The majority (89%) of the recovered flavonoids, however, was unchanged X. The remaining fraction consisted of small amounts of different metabolites, including some IX. Avula et al. (2004) [*J. Chromatogr. Sci.* 42:378-382], performed a similar experiment with rats and detected mainly unchanged X next to a number of unidentified metabolites.

The possibility that IX would act as a pro-estrogen was considered by Coldham et al. (2002) *Food Addit. Contam.* 19:1138-1147. The assumption was based on the extensive biotransformation capacity of the liver, which includes demethylation. However, the exposure of IX to liver microsomes did not lead to an increase in estrogenic activity, from which it was concluded that no 8-PN was produced. In contrast, Nicolic et al. describe that liver microsomes can demethylate IX, but not X (Nikolic et al. (2005) *J. of Mass Spectrom.* 40, 289-299). However, it was shown that, besides demethylation, microsomes also modify the prenyl side-chain, finally resulting in a large variety of minor degradation products. Schaefer et al. (2003) (*J. Steroid Biochem. Mol. Biol.* 84, 359-360), identified low levels of 8-PN in urine after oral intake of IX by two test persons and attributed this to demethylation by the liver.

Besides the liver, the colon is also an important transformation site in the human body. The human colon contains $\sim 10^{12}$ microorganisms/cm$^3$ (about 400 different species), with an enormous catalytic and hydrolytic potential. The importance of this microbial community in the metabolism of phytoestrogens in general has been clearly established. Wang et al. (2000) *Chem. Pharm. Bull.* 48, 1606-1610, identified two bacteria responsible for the transformation of lignans and Decroos et al. (2005) *Arch. Microbiol.* 183, 45-55, recently isolated a microbial consortium capable of transforming the soy phytoestrogen daidzein into equol]. Moreover, several intestinal bacteria were shown to enhance the bioavailability of phytoestrogens as they possess β-glucosidases, which are necessary for the hydrolysis of phytoestrogen glycosides (Rowland et al. (2003) *Br. J. Nutr* 89, s45-S58). Thus, the gut microbiota are considered to be a factor of importance for phytoestrogen bioavailability (Turner et al. (2003) *Nutr. Rev.* 61, 204-213).

As only the essential oil and the alpha-acids present in the female hop cones are of economic interest as important brewery ingredients, the different extraction methods of hop which have been developed aim to specifically extract only these compounds. On the one hand, $CO_2$ is currently the most accepted solvent for the manufacture of hop extracts (Palmer & Ting (1995) *Food Chem.* 52, 345-352). In comparison with the procedures that use conventional organic solvents (ethanol, hexane, methanol, or methylene chloride), $CO_2$-extraction provides more selective extracts that can be used for the production of beers as a good alternative for whole hops or hop pellets. $CO_2$-extracts form the basis of a large number of further derived and purified products, such as iso-alpha-acids and reduced derivatives. Another procedure for further purification of $CO_2$-extract, by removal of unwanted prenylflavonoids, is disclosed in U.S. Pat. No. 3,794,744.

On the other hand, different procedures have been developed to specifically recover and purify prenylflavonoids (mainly X). Examples of these extraction methods are disclosed in U.S. Pat. No. 4,121,040 and German patent DE19939350. As xanthohumol can easily be recovered using these processes, little interest has been shown in developing a procedure to chemically synthesize X. 8-PN, however, is more difficult to recover from natural extracts because of the low concentrations present in the hop cone. Therefore, synthesis strategies have been developed to produce 8-PN by prenylation of the commercially available naringenin. First, 8-PN is produced by the low yielding unselective direct C-prenylation of naringenin or starting from phloroacetophenone. Efficient small scale chemical synthesis was achieved by europium(III)-catalyzed Claisen rearrangement (Gester et al. (2001) *Tetrahedron* 57, 1015-1018). Recently, industrial scale production based on this method has been described in the European patent EP1524269.

Despite the widespread industrial use of hop and hop extracts, there is no efficient method for the production of bioactive prenylated phytoestrogens such as 8-PN from a natural source.

SUMMARY OF THE INVENTION

An object of the present invention is to provide an efficient method for the production of bioactive prenylated phytoestrogens such as 8-PN, from 5-alkoxyflavonoids, which can be obtained from a natural source, as well as pharmaceutical compounds and food supplements using such bioactive prenylated phytoestrogens.

In a first aspect, the present invention provides compositions having 5-alkoxy-flavonoid-transferase (5-AO-FT) and/or 6'-alkoxy-chalcone-transferase (6'-AO-CT) activity. More particularly the invention provides compositions having 5-methoxy-flavonoid-methyltransferase (5-MO-FMT) and/or 6'-methoxy-chalcone-methyltransferase (6'-MO-CMT) activity. A further embodiment of the present invention relates to compositions capable of dealkylating prenylated 5-alkoxy-flavonoids and/or prenylated 6'-alkoxy-chalcones. A specific embodiment of the invention provides compositions capable of dealkylating the 6'-alkoxychalcone xanthohumol (X) and/or the 5-alkoxy-flavonoid isoxanthohumol (IX). The compositions of the present invention thus are capable of producing bioactive phytoestrogens, more particularly prenylated phytoestrogens, more particularly 8-PN.

According to a particular embodiment, the compositions having 5-alkoxy-flavonoid- and/or 6'-alkoxy-chalcone-dealkylating activity are compositions comprising or derived from material of non-animal origin, more particularly of prokaryotic origin. More particularly, the compositions of the invention comprise bacterial cells, or extracts, supernatant or other purified or semi-purified material of such bacterial cells. A specific embodiment of the present invention relates to a composition comprising a homoacetogenic bacterium, such as a *Eubacterium* sp or *Peptostreptococcus* sp., most particularly a *Eubacterium limosum* or *Peptostreptococcus productus*, or extracts, supernatant or other purified or semipurified material therefrom.

Another particular embodiment of the invention comprises bacterial strains and or compositions comprising cells, extracts, supernatant or other purified or semi-purified material thereof, of which the production of 5-alkoxy-flavonoid-transferase (5-AO-FT) and/or 6'-alkoxy-chalcone-transferase (6'-AO-CT) activity has been enriched, more particularly by repeated incubations with a 5-alkoxyflavonoid, such as a 5-methoxy prenylflavonoid.

Yet another particular embodiment of the invention comprises compositions comprising a 5-methoxy-(prenyl)flavonoid methyltransferase and/or 6'-methoxy-(prenyl)chalcone methyltransferase from a homoacetogenic bacterial strain, more particularly from a *Eubacterium* sp., most particularly from *Eubacterium limosum*.

A particular embodiment of the compositions of the present invention relate to compositions comprising an enriched activity of 5-alkoxy-flavonoid-transferase (5-AO-FT) and/or 6'-alkoxy-chalcone-transferase (6'-AO-CT), derived from the bacterial strain of *Eubacterium limosum* deposited with the Belgian Coordinated collections of Microorganisms (BCCM) in the BCCM/LMG collection with deposit number LMG P-23546.

In a further aspect, the present invention provides methods for the production of phytoestrogens, comprising dealkylating 5-alkoxy-flavonoids at the 5 position or for dealkylating 6'-alkoxychalcones at the corresponding 6' position, characterized in that it is performed in vitro using non-animal eukaryotic or prokaryotic material. In a specific embodiment, the methods are used for the production of 8-PN.

According to a particular embodiment, the dealkylation in the methods of the invention is a demethylation and is performed using non-animal eukaryotic or prokaryotic material. More particularly, the non-animal material is a bacterial strain or material of a bacterial strain, most particularly of a homoacetogenic bacterium, or purified or partially purified fractions or components thereof, such as partially purified or isolated enzymes. A specific embodiment relates to a dealkylation using material from a *Eubacterium* sp. or a *Peptostreptococcus* sp., such as *Eubacterium limosum*. Further specific embodiments of the method of the invention include methods for dealkylating prenylated 5-alkoxy-flavonoids and/or prenylated 6'-alkoxy-chalcones.

According to a further specific embodiment, methods are provided for the dealkylation of 5-alkoxy-flavonoids and/or the 6-alkoxy-chalcones which are of plant origin, more specifically, which originate from hop. According to particular embodiments methods are provided for the dealkylation of the 6'-alkoxychalcone, xanthohumol and/or of the 5-alkoxy-flavonoid, isoxanthohumol.

A further aspect of the invention is the use of a bacterial cell line for the in vitro dealkylation of a 5-alkoxy-flavonoids and/or 6'-alkoxy-chalcones, more particularly for the demethylation of a 5-methoxy-flavonoids and/or 6'-methoxy-chalcones. More specifically, the bacterial cells are cells from a homoacetogenic bacterial strain, such as *Eubacterium limosum*. A further specific embodiment is the use of bacterial cells, in which the production of 5-alkoxy-flavonoid-transferase (5-AO-FT) and/or 6'-alkoxy-chalcone-transferase (6'-AO-CT) activity has been increased, e.g. by repeated incubations with a 5-alkoxyflavonoid, such as a 5-methoxy prenylflavonoid.

Yet a further aspect of the invention provides methods for producing phytoestrogens in vitro which comprise the steps of a) providing a bacterial strain of a bacterium, more particularly a homoacetogenic bacterium or extracts thereof and b) contacting a composition comprising 5-alkoxy-flavonoids, more particularly 5-methoxy-flavonoids and/or 6'-alkoxy-chalcones more particularly 6'-metoxy-chalcones with the bacterial strain or an extract thereof so as to allow dealkylation of the 5-alkoxy-flavonoids and/or 6'-alkoxy-chalcones by the bacterial strain or extract thereof. Optionally, the methods further comprise identifying and/or purifying the dealkylated flavonoid produced.

Specific embodiments of these methods are methods which include the provision of an extract of a bacterial strain, which further include the step of enriching and optionally purifying the bacterial extract so as to contain enriched or purified 5-alkoxy-flavonoid-transferase (5-AO-FT) activity and/or enriched or purified 6'-alkoxy-chalcone-transferase (6'-AO-CT) activity.

Additionally or alternatively the methods of the present invention include the step of enriching the production of the bacterial strain of 5-AO-FT and/or 6'-AO-CT activity, by repeated incubations with a 5-alkoxyflavonoid, such as a 5-methoxy prenylflavonoid.

Yet another aspect of the invention provides a 5-methoxy-prenylflavonoid methyltransferase or 6'-methoxy-prenylchalcone methyltransferase from *Eubacterium limosum*.

Yet another aspect of the invention provides pharmaceutical compositions and food supplements comprising the bioactive phytoestrogens obtained by the methods of the present invention Yet another aspect of the present invention provides pharmaceutical compositions and food supplements comprising two components for simultaneous or consecutive administration, wherein the first component comprises a homoacetogenic bacteria, or an extract or component thereof having 5-alkoxy-flavonoid-transferase (5-AO-FT) and/or 6'-alkoxy-chalcone-transferase (6'-AO-CT) activity and the second component comprising 5-alkoxyflavonoids or 6'-alkoxychalcones or a source thereof, such as a hop extract. According to particular embodiments the flavonoid is the 6'-alkoxychalcone xanthohumol or the 5-alkoxy-flavonoid isoxanthohumol. Further particular embodiments relate to pharmaceutical compositions and food supplements according to the invention wherein the homoacetogenic bacterium is *Eubacterium limosum*. Optionally the bacteria in the pharmaceutical composition of the invention are provided in a formulation for colon specific delivery.

The present invention discloses that IX can be demethylated into 8-PN by non-animal living organisms such as bacteria of the human or animal, especially vertebrate or mammal, intestine and that IX can thus act as pro-estrogen. The present invention further identifies microorganisms, capable of performing the conversion of IX into 8-PN, e.g. the in-vitro production of 8-PN, using cultures of such microorganisms. Additionally, the present invention provides methods for the selection of other strains, capable of quantitatively producing 8-PN from IX.

The present invention further demonstrates that the conversion of methylated flavonoid phytoestrogen precursors by microbial flora in vivo is very variable and depends on the composition of the microbial flora in the individual (between individuals or within the same individual at different moments). This is likely to have important consequences on the exposure of individuals to phytoestrogens. Indeed, in hop extracts, in beer and in food products or supplements, IX, which is less estrogenic, is present in much higher concentrations than 8-PN.

By presenting methods for the production of activated phytoestrogens (in vitro or in vivo), the present invention further provides an interesting alternative or complement to the current dietary hop extracts. The unpredictable yield of conversion of methylated flavonoid phytoestrogen precursors (e.g. IX) into their active demethylated compounds can be controlled by in-vitro pre-conversion or in vivo/in situ dealkylation. This makes it possible to control the exposure to the active component in each individual, despite the individual differences in intestinal microflora, or to specifically take these differences into account.

DETAILED DESCRIPTION OF THE INVENTION

The Figures are intended to illustrate the present invention but should not be considered as implying any limitation of the invention to the embodiments presented therein.

FIG. 1: General structures of flavonoids.

Figure 2:
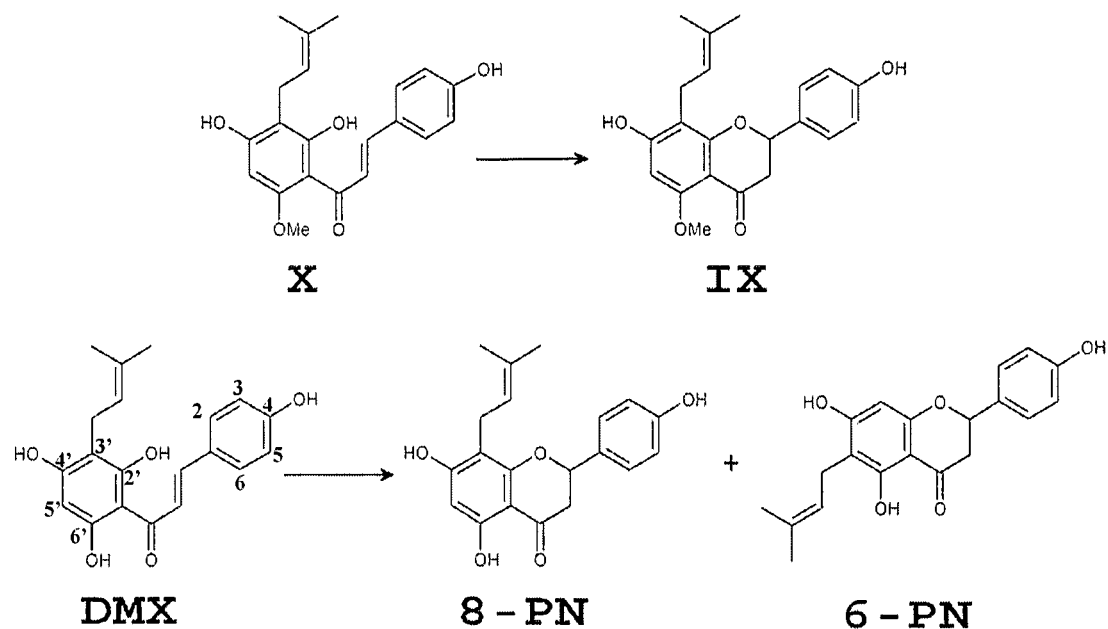

FIG. 2: Structures of hop prenylflavonoids and their conversion.

Figure 3:
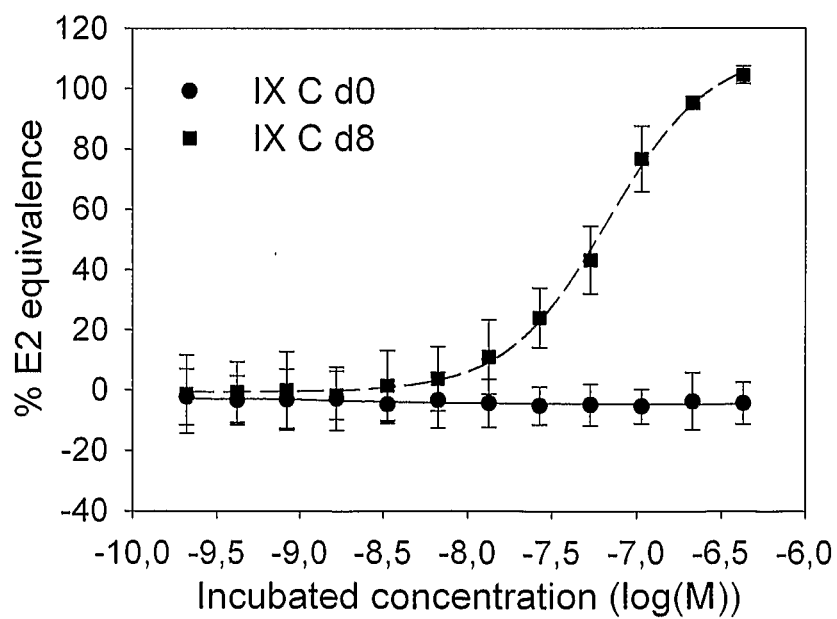

FIG. 3: Estrogen response (average+st. dev.) of a fecal culture (C) incubated with IX (0 and 8 days of incubation) (n=3).

Figure 4:
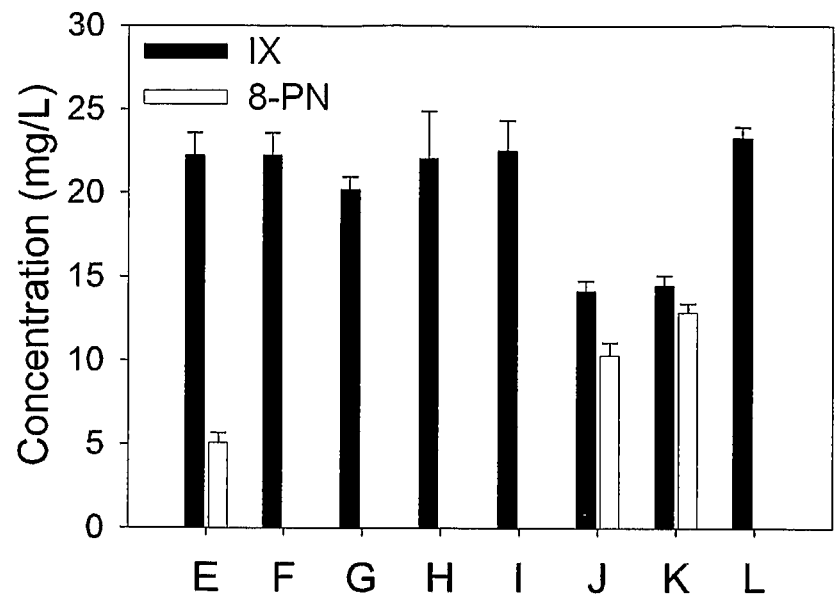

FIG. 4: Transformation of IX (25 mg/l) by human fecal cultures (E-L) into 8-PN after 3 days [average+st. dev. (n=3)].

Figure 5:
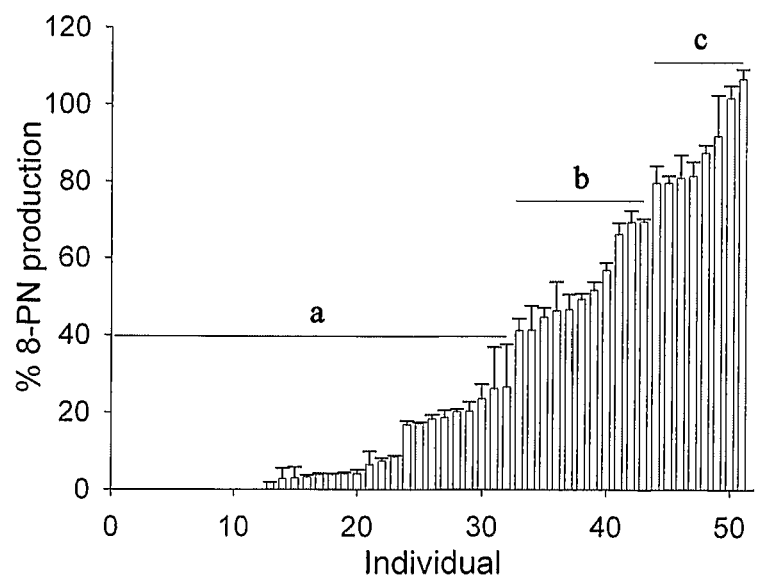

FIG. 5: Conversion of isoxanthohumol (IX) into 8-prenylnaringenin (8-PN) by intestinal bacteria from 51 different human individuals. The individuals were arranged by increasing 8-PN production and results are presented as mean % (±SD) IX conversion into 8-PN (n=3).

Figure 6:
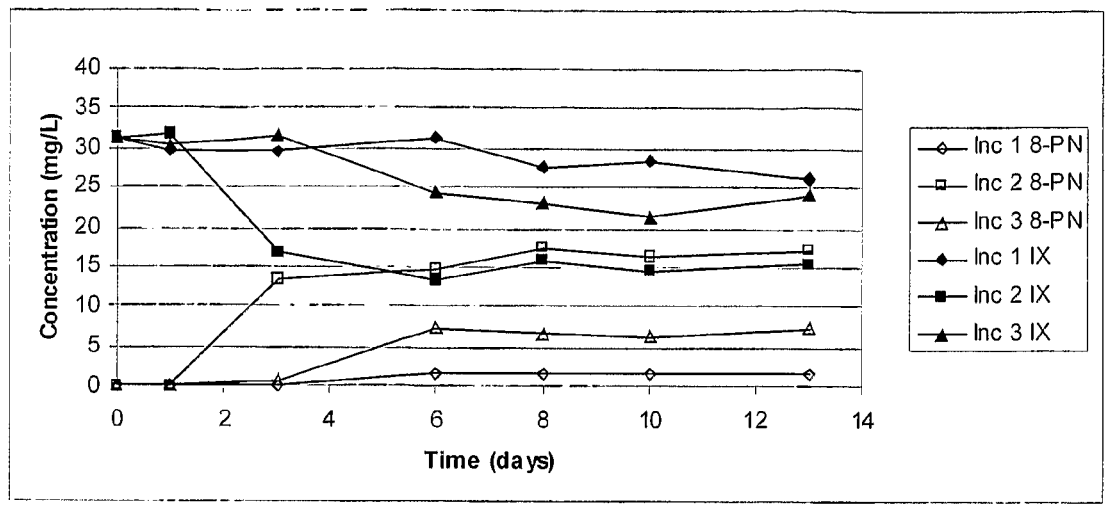

FIG. 6: Conversion of IX (25 mg/l) by *P. productus* into 8-PN (three cultures: Inc I, Inc 2 and Inc3). Disappearance of IX (filled symbols) and production of 8-PN (open symbols) were monitored over a period of 13 days.

Figure 7:
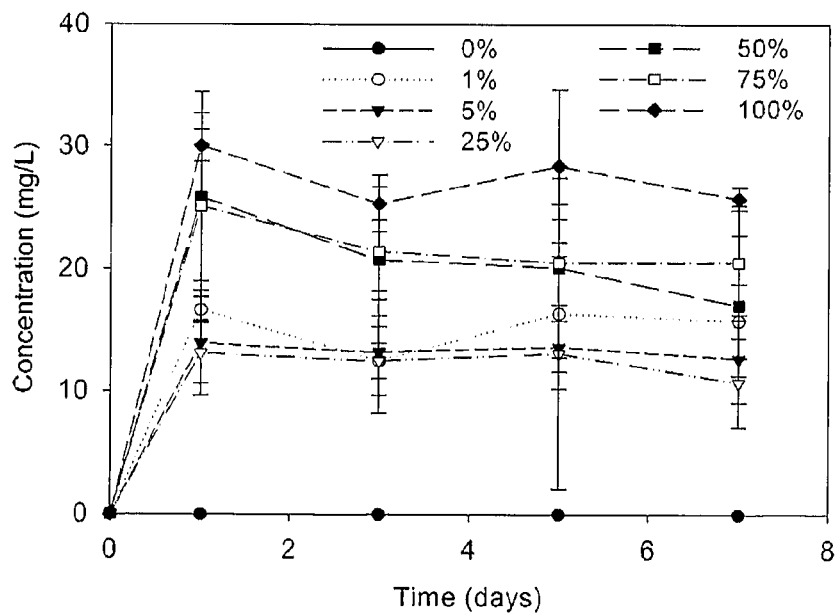

FIG. 7: Conversion of IX in to 8-PN after supplementation of a *E. limosum* culture to fecal culture B (percentage of *E. limosum* culture from 0% (solely fecal sample) up to 100% (axenic *E. limosum* culture)) (n=3).

Figure 8:
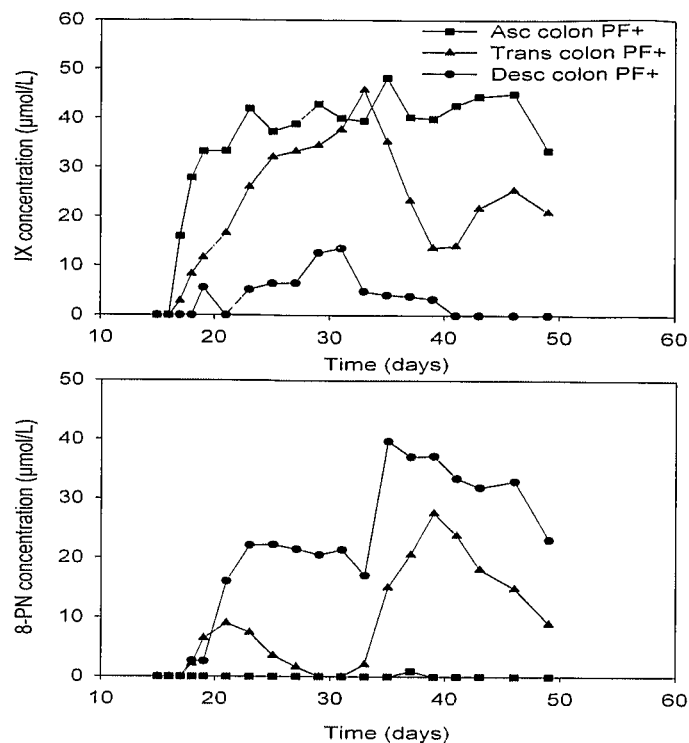

FIG. 8: Conversion of IX into 8-PN in a simulator of the human intestine microbial ecosystem in under conditions allowing the activation of methylated methylflavonoids. the PF+ compartment of the TWIN SHIME.

Figure 9:
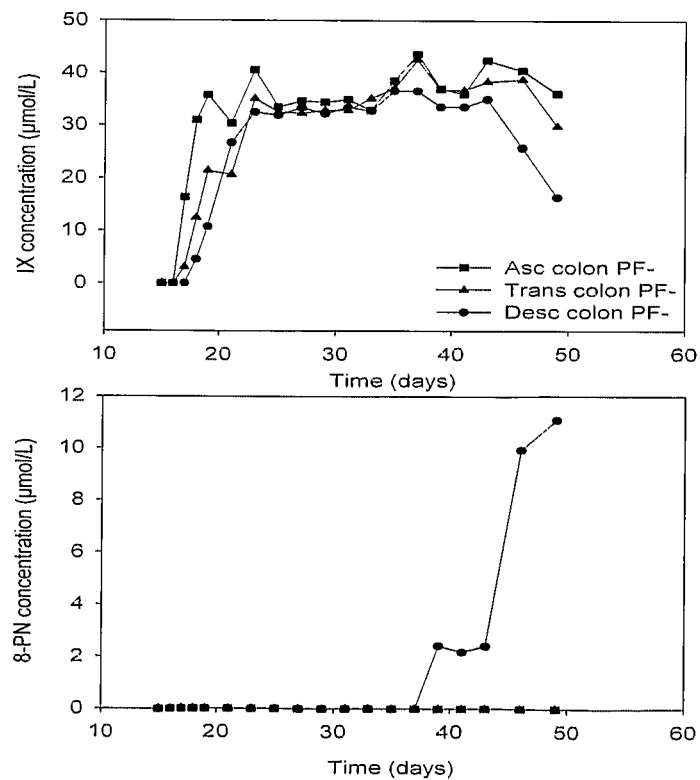

FIG. 9: Conversion of IX into 8-PN in a simulator of the human intestine microbial ecosystem in under conditions not allowing the activation methylated methylflavonoids.

DEFINITIONS

Throughout the present application, the following abbreviations are used:
X: xanthohumol;
DMX: desmethylxanthohumol;
IX: isoxanthohumol;
8-PN: 8-prenylnaringenin;
6-PN: 6-prenylnaringenin
5-AO-FT: 5-alkoxyflavonoid alkyltransferase
5-MO-FMT: 5-methoxy-flavonoid methyltransferase
6'-AO-CT: 6'-alkoxychalcone alkyltransferase
6'-MO-CMT: 6'-methoxy-chalcone methyltransferase The term "flavonoids" refers to a group of organic molecules based on a $C_{15}$ skeleton with a chromane ring bearing a second aromatic ring B in position 2, 3 or 4. (FIG. 1A). FIG. 1A shows the conventional numbering for substituents on flavonoids, which is also used in the present invention. Subgroups of flavonoids are chalcones, flavanones, flavones, flavanols and isoflavonoids. Chalcones (FIG. 1B) are isomers of flavanones (FIG. 1C). FIGS. 1B and 2 show the conventional numbering of chalcones. The flavanones differ from flavones (FIG. 1E), in that they lack the double bond in the 2,3 position. Flavones (FIG. 1E) are flavonoids lacking the 3-OH group of flavanols (FIG. 1E). The isoflavonoids are flavonoids wherein the phenylring B is located at the 3 position (FIG. 1F). All these subgroups have a keto function at the 4 position.

The term "prenylflavonoid" as used in the present invention relates to a flavonoid containing an apolar prenyl-side chain attached to one of the phenolic rings. The prenyl chain mostly occurs at the 8 position but can also be at the 6 position, or at both the 6 and the 8 position [in chalcones the prenyl chain is located at the 3' and/or 5' position]. In hop, prenylflavonoids are mainly found in the lupulin glands, found at the base of the bracteoles in the hop cones of the female plant. Other natural sources of prenylflavonoids are for example *Dendrolobium lanceolatum, Sophora flavescens, Sophora tomentosa, Artocarpus communus* and *Marshallia grandiflora*. Examples of prenylflavonoids are chalcones (such as xanthohumol (X) and desmethylxanthohumol (DMX), dehydrocycloxanthohumol) and flavanones (such as isoxanthohumol (IX), 8-prenylnaringenin (8-PN) and 6-prenylnaringenin (6-PN).

The term "geranylflavonoid" relates to a flavonoid containing an apolar geranyl-side chain attached to one of the phenolic rings. Examples are tetrahydroxy-geranylchalcone, 6-geranylnaringenin, 3'-geranylchalconaringenin and 8-geranylnaringenin. All these geranylated compounds have been isolated from hop cones and 8-geranylnaringenin has alleged estrogenic activity (Milligan et al. (2000) *J. Clin. Endocrinol. Metab.* 85, 4912-4915).

The term "enzymatic dealkylation or demethylation" as used herein refers to the removal of an alkyl or a methyl group, respectively, from a compound by use of an enzyme.

The term "5-alkoxy dealkylation" or "5-methoxy demethylation", as used herein refers to the removal of an alkyl group from an alkoxy group or a methyl from a methoxy (—$OCH_3$) group, respectively, located at the 5 position of a flavonoid (for ring numbering see FIG. 1A). In this context "5-methoxy" and "5-O-methyl-" have the same meaning.

The term "5-alkoxy-(prenyl)flavonoid transferase (5-AO-(P)FT)" refers to the enzyme capable of ensuring the 5-alkoxy dealkylation of 5-alkoxy-(prenyl)flavonoids.

A particular group of flavonoids are chalcones wherein the ring numbering is different. Thus with respect to chalcones, the present invention relates to the removal of an alkyl group from a chalcone compound, most particularly 6'-alkoxy demethylation, i.e. the removal of an methyl group from an alkoxy group, such as a methoxy (—$OCH_3$) located at the 6' position of a chalcone (for ring numbering see FIG. 1B). Herein "6'-methoxy" and "6'-O-methyl-" have the same meaning. The enzyme ensuring the 6'-alkoxy dealkylation and more particularly the 6'-methoxy-demethylation are also referred to as "6'-alkoxy-(prenyl)chalcone transferase (6'-AO-(P)CT)" and "6-methoxy-(prenyl)chalcone methyltransferase (6'MO(P)C MT)", respectively.

The term "micro-organism" as used herein includes both bacteria and fungi. It relates to strains of individual micro-organisms, microbial consortia or microbial communities, such as the microbial community of the animal intestine or of any other part of animals (including humans), or from any environmental sample.

The term "in-vitro method" used in the context of the present invention relates to methods performed outside multicellular organisms and includes both methods performed in the absence of living cells (making use of e.g. lysed cells, protein extracts or recombinant proteins) and processes performed using living cells, more particularly cultures of isolated cells. When referring to in vitro methods it is thus intended to exclude processes such as occurring in nature in intact hop cones or in the intestines of living animals.

When referring to 'in-situ' dealkylation', the demethylation activity in vivo, in one or more specific organs of the body is intended.

When referring to 'bacteria' herein, both aerobic or anaerobic bacteria are intended.

"Homoacetogens" in the context of bacteria are anaerobic bacteria that reduce $CO_2$ to acetate or to oxidised acetate via the acetyl-CoA pathway. Representative homoacetogenic bacteria are, for example, *Acetoanaerobium noterae, Acetobacterium woodii, Acetobacterium wieringae, Acetogenum kivui, Acetitomaculum ruminis, Clostridium aceticum, Clostridium thermoaceticum, Clostridium formicoaceticum, Desulfotomaculum orientis, Sporomusa paucivorans, Peptostreptococcus* sp. and *Eubacterium* sp.

The terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

According to the present invention, enzymatic dealkylation, and more particularly the 5-alkoxy dealkylation of flavonoids can be achieved by enzymes generally referred to as 5-alkoxy-transferases, more particularly by a 5-methoxy flavonoid methyltransferase (5-MO-FMT) and/or a 6'-methoxychalcone methyltransferase (6'-MO-CMT) as well as by an intact living or inactivated cell (or cellular material) producing the 5-alkoxy-flavonoid alkyltransferase or 6'-alkoxychalcone alkyltransferase enzyme, by a lysate of such a cell, by a fraction of a lysate of such a cell (for example, the membrane or the cytoplasm), by an enriched or purified protein fraction comprising said 5-alkoxy-flavonoid alkyltransferase and/or 6'-alkoxychalcone alkyltransferase, or by a recombinant expressed 5-alkoxy-flavonoid alkyltransferase and/or 6'-alkoxychalcone alkyltransferase. Where the recombinant dealkylating enzyme is secreted by the cells, a conditioned medium can be used. Where the recombinant enzyme is cytoplasmic, secretion signals can be added to the recombinant DNA to obtain a protein which can be harvested from its growth medium.

The invention provides alkoxy-dealkylases, more particularly enzymes capable of removing an alkyl group from an alkoxyflavonoid. The alkyl group can be a linear or a branched alkyl. More particularly the alkyl group is a $C_1$-$C_6$ alkyl. In a specific embodiment, the alkyl is a methyl.

According to the present invention, 5-alkoxy-alkyltransferases, more particularly 5-alkoxy-flaonoid-alkyltransferases are provided which are of prokaryotic or eukaryotic non-animal origin, including 5-alkoxy-alkyltransferases originating from a plant cell or a micro-organism.

A first aspect of the invention relates to cells, extracts, and enriched, semi-purified or purified proteins (as well as to compositions comprising one or more of these) capable of dealkylating 5-alkoxy-flavonoids, more particularly capable of demethylating 5-methoxy flavonoids and/or 6'-methoxy chalcones. According to a particular embodiment of the present invention, the cells, extracts and proteins comprising 5-AO-FMT (and/or 6'-AO-CMT) activity are of bacterial origin. Most particularly, the bacteria are homoacetogenic bacteria. A further embodiment of the invention relates to homoacetogenic bacteria selected from the species *Eubacterium* and *Peptostreptococcus*. Homoacetogenic bacteria can be cultivated under anaerobic conditions with sugars, one-carbon compounds such as formate, methanol, CO and $CO_2$ plus $H_2$ as well as alkoxylated aromatic compounds as carbon source. Bacterial strains with increased or enriched prenylflavonoid dealkylating or demethylating activity can be obtained by selection based on repeated inoculation on a relevant substrate, as described in the examples section herein. The enrichment of activity as referred to herein relates to activity being between about 1.5 and about 10 times higher than the original strain, more particularly being about 3 times higher than the original strain. Additionally or alternatively, the enrichment method of the present invention ensures an enzymatic activity which reaches up to between 90-100% conversion of the substrate (using e.g. 25 mg/l IX). Thus, the present invention also relates to methods for enriching the 5-alkoxy-flavonoid-transferase (5-AO-FT) and/or 6'-alkoxy-chalcone-transferase (6'-AO-CT) activity of bacterial strains, comprising the step of incubating the strain on a medium with a 5-alkoxyflavonoid, such as a 5-methoxy prenylflavonoid (or a 6'-methoxychalcone), more particularly comprising the step of spreading the bacterium on a medium comprising IX (or X), followed by selection of the strongest producing colony. Most particularly the strain is repeatedly spread out on a medium comprising the substrate, such as 2-10 times, more particularly 3 or 4 times, followed by selection of the colony with the highest 5-alkoxy-flavonoid-transferase (5-AO-FT) and/or 6'-alkoxy-chalcone-transferase (6'-AO-CT) activity. This activity can be measured e.g. based on the production of the end product of the reaction. According to a particular embodiment, this method of enrichment is performed on a homoacetogenic bacterial strain, more particularly a strain of *Eubacterium* or *Peptostreptococcus*, most particularly *E. limosum* or *P. productus*. A specific example of a bacterial strain which has been enriched *Eubacterium limosum* has been deposited with the Belgian Coordinated collections of Microorganisms (BCCM) in the BCCM/LMG collection, Laboratorium voor Microbiologie, Universiteit Gent (UGent), K. L. Ledeganckstraat 35, B-9000 Gent, Belgium, with deposit number LMG P-23546 on Mar. 15, 2006, by Willy Verstraete.

Thus, the present invention provides a method for producing enriched, semi-purified and/or purified 5-alkoxy flavonoid transferase, more particularly 5-methoxy-prenylflavonoid methyltransferase, which method comprises the steps of obtaining a bacterial strain, more particularly a strain of a homoacetogen, such as *Eubacterium limosum* with increased/enriched 5AO-FT activity, more particularly increased 5MO-FMT activity and enriching, semi-purifying or purifying the enzyme using classical purification methods, including precipitation by ammonium sulphate, ion-exchange chromatography and gel filtration chromatography.

The bacterial strains of the present invention provide a source wherein the alkyl- or methyltransferase is present in high concentrations and/or wherein a naturally occurring mutant with high activity is present. In both cases, reference is made to an 'enriched' bacterial strain.

According to yet another embodiment of the invention, the cell comprising 5-alkoxy dealkylating activity, more particularly 5-methoxyflavonoid-demethylating activity (and/or 6'-methoxychalcone-demethylating activity) is a transgenic cell obtained by the introduction of a DNA sequence encoding a 5-alkoxy-alkyltransferase, more particularly 5-MO-FMT (and/or 6'-MO-CMT) into a microorganism or plant cell. Genetically modified plant cells with increased 5-MO-FMT (and/or 6'-MO-CMT) activity can also be grown into plants with increased 5-MO-FMT (and/or 6'-MO-CMT) activity, which can be combined with natural or artificially induced high alkoxyflavonoid (e.g. methylflavonoid) levels resulting in 'in planta' production of phytoestrogens. Thus, the present invention provides genetically modified plants, such as, but not limited to, hop plants, with increased phytoestrogen content.

According to another embodiment, the cells, extracts and proteins comprising 5-alkoxy dealkylating activity, more particularly 5-methoxy demethylating activity, are plant cells of *Humulus lupulus* or of other plants wherein 8-PN is synthesized such as *Marshallia grandiflora* and *Sophora tomentosa*. For conversion on a higher scale, plants can be screened wherein the natural conversion of X or IX into 8-PN is enhanced, in order to find natural mutants of the 5-MO-FMT (and/or 6'-MO-CMT), or overexpressing 5-MO-FMT (and/or 6'-MO-CMT).

Cells or compositions can be assayed for 5-AO-FT (and/or 6'-AO-CT), or more specifically 5-MO-FMT (6'-MO-CMT) activity using an assay wherein the conversion of a 5-O-methylated flavonoid (6'-O-methylated chalcone) test substrate into its demethylated form is investigated. The test substrate is preferably a prenylated 5-methoxyflavonoid. According to a particular embodiment compound IX is used as a substrate and the conversion into 8-PN is assayed by mass spectrometry, HPLC or another analytical method. The enzyme specificity of a cell, extract or composition comprising 5-methoxy demethylating activity can be assayed by using a flavonoid substrate with methoxygroups on other positions. For instance, an appropriate substrate for assaying is tangeretin which has methoxy groups at positions 4', 5, 6, 7 and 8. This assay allows to discriminate between the dealkylating activity of 5-AO-FT (and/or 6'-AO-CT) or demethylating activity of 5-MO-FMT (and/or 6'-MO-CMT) of bacterial origin and the demethylating activity of mammalian microsomes or from plant cells. Extracts of the bacterial or plant cells retaining 5-methoxy-demethylating activity are obtained by standard protein extraction methods. Purified proteins having 5-MO-FMT (and/or 6'-MO-CMT) activity are obtained by protein purification methods coupled with activity screening of purified fractions.

A second aspect of the invention relates to the use of bacteria producing a 5-alkoxy flavonoid transferase (5-AO-FT) and/or 6'-alkoxy chalcone transferase (6'AO-CT), or more specifically, a 5-methoxy flavonoid methyltransferase (5-MO-FMT) and/or 6'-methoxy chalcone methyltransferase (6'-MO-CMT), or extracts or purified proteins thereof comprising this activity for the dealkylation or demethylation of naturally occurring and synthetic 5-methoxyflavonoids, including prenylated or geranylated 5-methoxyflavonoids.

In a particular embodiment of the invention, cells, more particularly microorganisms, capable of converting 5-methylated flavonoids such as IX into 8-PN are used for the cost-efficient in-vitro production of 8-PN and related compounds. Different embodiments are envisaged such as: the incubation of e.g. a bacterial demethylating strain with hop extracts or (partially) purified hop-derived compounds; the spraying of e.g. a bacterial demethylating strain, cellular extract or eventually conditioned medium over hop extracts or (partially) purified hop-derived compounds; or submerging the latter in medium containing a strain of e.g. demethylating bacteria or, cellular extract or eventually conditioned medium, possibly followed by inactivation of the strain after a certain time. Thus, the present invention also provides methods for the large scale cost-efficient in-vitro production of phytoestrogens.

According to the present invention, 5-AO-FT (and/or 6'-MO-CT)-activity containing bacteria, extracts and/or proteins can be used for the production of active estrogens, more particularly phytoestrogens from 5-alkoxyflavonoids. One particular embodiment of the present invention relates to the use of 5-MO-FMT and/or 6'-MO-CMT activity in the demethylation of plant flavonoids, more particularly flavonoids obtainable from hop (*Humulus lupulus*). A further specific embodiment of the present invention relates to the conversion of IX into 8-PN, or the demethylation of derivatives of IX to derivatives of 8-PN, having essentially the same biological activity. According to a particular embodiment certain derivatives of demethylated prenylflavonoids such as 8-PN can be generated by first modifying the structure of an easily available methylated precursor, followed by the demethylation in accordance with the present invention whereby demethylated prenylflavonoid derivatives are obtained. Possible modifications are such as the addition of side chains or saturation or desaturation of bonds.

Moreover, the 5-AO-FT and/or 6'-AO-CT, more specifically the 5-MO-FMT and/or 6'-MO-CMT activity containing cells and extracts of the present invention can be used for the dealkylation of other 5-alkoxyflavonoids. Most particularly other 5-methoxyflavonoids (or 6'-methoxychalcones) than IX (or X) are also envisaged as substrates according to the present invention, such as 5-methoxyflavonoids or 6'-methoxychalcones having substituents at the 4, 6, 7, 8, 2', 3', 4', 5' and 6' (flavonoid numbering) each independently selected from the group consisting of H, $C_1$-$C_6$ alkyl, $C_1$-$C_6$ alkoxy and $C_1$-$C_6$ acyl, halogens, longer C-chains, aromatics, one or more sugar residue(s) or sugar alcohols, ethers, esters, phosphates, sulfates, amines, etc.

According to a particular embodiment of the invention, the 5-alkoxyflavonoid, more particularly the 5-methoxyflavonoid is characterized by a hydroxyl group at the 7 position and/or a double bond between the 2 and 3 position and/or a hydroxyl group at the 4' position. Most particularly, the present invention relates to the use of the 5-MO-FMT activity in the demethylation of 5-methoxyflavonoid compounds comprising a prenyl or geranyl group at the 6 and/or the 8 position. Optionally, this prenyl or geranyl group can be further modified by modifications such as but not limited to modification of the double bond, transformation into isoprenoid and substitutions. In certain embodiments these 5-methoxyflavonoids are 6'-methoxychalcones or 5-methoxyflavanones, including prenylated or geranylated versions thereof. In particular embodiments they are selected from the group of xanthohumol (X) (2',4,4'-trihydroxy-3'-prenyl-6'-methoxychalcone) (the numbering of chalcones is indicated in FIG. 1B and FIG. 2) and isoxanthohumol (IX) (5-O-methyl-8-prenylnaringenin), or derivatives thereof, with essentially similar biological activity (or whereby demethylation of these compounds results in a compound with essentially similar biological activity).

Another embodiment of the present invention relates to the use of bacteria, or extracts thereof comprising 5-alkoxy flavonoid transferase (5AO-FT) and/or 6'-alkoxy chalcone transferase (6'AO-CT) activity in the dealkylation of compounds selected from the group of the following molecules having, in addition a 5-methoxygroup: 4'-acetyl-7-prenyloxynaringenin, (±)-(E)-8-(4''-hydroxyisopentenyl)naringenin (8-PN-OH), (±)-(E)-8-(4''-oxoisopentenyl)naringenin (8-PN=O) and 6,8-diprenylnaringenin.

The present invention provides improved methods of producing demethylated prenylflavonoids in vitro using non-animal eukaryotic or prokaryotic material. This is of particular interest for those demethylated prenylflavonoids which are of commercial value, such as 8-PN. As mentioned above, 8-PN shows in vivo estrogenic activity, prevents bone loss, inhibits angiogenesis and metastasis and exhibits anti-androgenic activity. Consequently, the compounds produced by the methods of the present invention can be used to treat or prevent disorders such as osteoporosis and cancer. The demethylated prenylflavonoids or geranylflavonoids with estrogenic properties, as obtained with the methods of the present invention, can be included in food products or food supplements for human or animal consumption, such as beverages, including beer, but also in cosmetics to be used on human or animal skin. Thus, the present invention further provides improved methods for the production of such food products or food supplements and pharmaceuticals.

Another aspect of the present invention relates to the in situ activation of methylated flavonoids in the intestine or any other part of the human or animal body, by administering cells, cell extracts or purified enzymes with 5-MO-FMT or 6'-MO-CMT activity. According to a particular embodiment the administration of 5-MO-FMT and/or 6'-MO-CMT activity is combined with the administration of methylated flavonoids, or a source thereof, separately or in one composition, at the same moment or consecutively. Both the composition comprising the enzymatic activity and the composition comprising the substrate can be provided as a pharmaceutical composition or a food supplement. Sources of methylated flavonoids include but are not limited to plant (e.g. hop) parts or extracts or purified methylated flavonoid compounds. The in situ production of demethylated prenylflavonoids, more particularly of 8-PN provides an alternative method of treatment and/or prevention for diseases and conditions which can be treated with estrogens, such as, but not limited to, bone loss, pathological angiogenesis, metastasis and as an antiandrogenic therapy.

Optionally, different administration strategies can be envisaged to specifically target alkylated flavonoids to the large intestine. This can be achieved for example by encapsulation of the composition which leads to the release in the large intestine or by conjugation to obtain a conjugate selected from the group consisting of glucuronide, sulfate, acetate, propionate, glucoside, acetyl-glucoside, malonyl-glucoside, and mixtures thereof.

In another aspect the present invention relates to a pharmaceutical composition and/or food supplement comprising or consisting of a cell, extract or purified protein thereof having 5-MO-FMT and/or 6'-MO-CMT) activity. According to a particular embodiment of this aspect of the invention, the cell is a cell of a micro-organism, more particularly a bacterial cell of a homoacetogen, such as the homoacetogens *Eubacterium* and *Peptostreptococcus*. Optionally the pharmaceutical compositions or food supplements further comprises a source of methylated prenylflavonoids or geranylflavonoids, which as demethylated compounds display strong estrogenic activity. Such a source can be a plant extract (especially hop), or an enriched fraction thereof. It can also be a synthetic methylated prenylflavonoid. Both the microorganisms and the methylated flavonoids can be provided in/with separate pharmaceutical carriers for simultaneous or sequential administration, or can be combined in the same pharmaceutical carrier, homogeneously distributed or asymetrically distributed, Accordingly, the invention provides combinations of pharmaceutical compositions, combinations of pharmaceutical compositions and food supplements, and combinations of food supplements. Moreover, the present invention provides methods of treatment comprising the steps of consecutive or simultaneous administration of the pharmaceutical compositions of the present invention to a patient in need thereof. In the same way, the present invention provides the use of the compositions comprising 5-alkoxy-alkyltransferase activity and/or the compositions comprising 5-alkoxyflavonoids described herein, for the manufacture of a medicament. Typically, the compositions of the present invention are administered as estrogen-supplements and/or estrogen replacement therapy to a patient in need thereof.

The amount of methylated IX or X (which will be demethylated into 8-PN) to be administered ranges between 10 and 20000 microgram/day/75 kg, between 50 and 10000 microgram/day/75 kg or between 50 and 7000 microgram/day/75 kg, for example about 5, 10 or 20 milligram/day/75 kg. Methylated forms of less potent flavonoids can be administered accordingly in higher doses after comparison of the estrogenic activity of this demethylated form with 8-PN.

One aspect of the present invention provides a pharmaceutical composition comprising the bacterium or bacterial extract having the 5-alkoxy-alkyltransferase activity of the present invention and a pharmaceutical carrier. In order to achieve optimal efficacy, the pharmaceutical carrier preferably releases the microorganisms to the colon. Colon targeted administration of medicaments is well known, and is reviewed for example in Chourasia & Jain (2004) *Drug. Deliv.* 11(2), 129-148. Various strategies, currently available to target the release of drugs to colon, include formation of prodrug, coating of pH-sensitive polymers, use of colon-specific biodegradable polymers, timed released systems, osmotic systems, and pressure controlled drug delivery systems. Among the different approaches to achieve targeted drug release to the colon, the use of polymers especially biodegradable by colonic bacteria holds great promise. Polysaccharidases are bacterial enzymes that are available in sufficient quantity to be exploited in colon targeting of drugs. Based on this approach, various polysaccharides have been investigated for colon-specific drug release. These polysaccharides include pectin, guar gum, amylose, inulin, dextran, chitosan, and chondroitin sulphate. This family of natural polymers has an appeal to drug delivery as it is comprised of polymers with a large number of derivatizable groups, a wide range of molecular weights, varying chemical compositions, and, for the most part, low toxicity and biodegradability yet high stability. The most favorable property of these materials is their approval as pharmaceutical excipients.

To prevent degradation from the interior side by the dealkylating bacteria of the present invention, the bacteria can be first placed in a non-bacterially degradable pharmaceutical carrier and then coated with a polymer which can be degraded by the microbial flora in the colon. Hereafter the bacteria can be released, e.g. by pH-controlled and time-controlled drug release mechanisms, or by taking advantage of the increase of the luminal pressure in the colon due to strong peristaltic waves as reviewed in Leopold (1999) *Med Klin.* 94 Suppl 1, 6-11.

Colon specific delivery systems which do not rely on the enzymatic activity of intestinal micro-organisms are also known. For example, the European patent EP0673645 describes a delivery system for targeting drugs to the colon, comprising three parts: (1) an enteric coating to prevent penetration of gastric fluid into the delivery system, thereby preventing any drug release in the stomach; (2) an erodible polymer layer which is exposed and gradually erodes during transit through the upper intestinal tract, and (3) a core, which is a conventional tablet or beadlet containing an active ingredient(s), which readily disintegrates and subsequently releases the drug to the target site, the colon, after erosion of the erodible polymer layer.

European patent application EP0453001 describes pharmaceutical compositions with the property of targeted controlled release of active principles which act pharmacologically within the intestine and in particular within the colon and the terminal portion of the ileum. The active principle is prepared in multi-particle multi-dose form and is covered with at least two membranes, one of pH-dependent solubility and the other insoluble but permeable to the intestinal fluids. While the covered active principle remains in the stomach and in the initial intestinal portion, i.e. while the pH is less than 5.5, it is not released. Only when it reaches an environment of higher pH (small intestine or colon) does the pH-dependent membrane dissolve to commence release of the active principle. From this moment the second membrane, which is pH-independent but permeable to the intestinal fluids, acts to slow down and control the dissolution of the medicament within the small intestine-colon tract.

EP0778778 describes a composition with one or more probiotic microorganisms such as *Eubacterium* and a carrier to transport the microorganisms to the large bowel. The carrier is a modified or unmodified resistant starch, particularly a high amylose starch, which acts as a growth or maintenance medium for microorganisms in the large bowel. US patent application 2004175389 discloses a formulation for preserving the life of probiotic bacteria during passage through the stomach, while permitting their release in the intestine, and particularly within the colon, and which has a low water activity and correspondingly long shelf life. The formulation includes a substantially water-free mixture of probiotic bacteria with monovalent alginate salts, wherein the mixture has been formed and is maintained in a substantially water-free environment. The alginate salts include sodium alginate and potassium alginate, but not divalent salts such as magnesium alginate or calcium alginate. Generally, and enteric coating (e.g., gelatin or cellulose encapsulation) for the formulation is provided.

It is to be understood that although particular embodiments, specific constructions and configurations, as well as materials, are discussed in the following examples section, these are only illustrative and various changes or modifications in form and detail may be made without departing from the scope and spirit of this invention.

EXAMPLES

Example 1

Demethylation of Isoxanthohumol (IX) by Human Fecal Cultures

Fecal samples were obtained from 12 healthy human subjects between the age of 20 and 35 and designated A to L. None of the subjects had a history of gastrointestinal disease and the subjects had not taken antibiotics in the 3 months prior to sample delivery. Fecal slurries of 20% (w/v) fresh fecal samples were prepared by homogenizing the feces with phosphate buffered saline (0.1 M, pH 7) containing 1 g/l sodiumthioglycolate as reducing agent. The particulate material was removed by centrifugation (1 min, 500×g). The supernatant is hereafter called "the culture".

The capacity of the cultures obtained from fecal samples A, B, C and D (further referred as cultures A-D) to degrade or transform the hop prenylflavonoid IX was tested by incubating the fecal cultures (10% (v/v)) in Brain Heart Infusion broth (with 0.5 g/l cystein-HCl) with 25 mg/l of isoxanthohumol for a period of 8 days under anaerobic conditions. Extracts of the incubations at days 0 and 8 were assayed for bioactive transformation products of IX using a Yeast Estrogenic Screen, according to De Boever et al. (2001) Env. Health Perspectives 109, 691-697, based on Routledge & Sumpter (1996) Environ. Toxicol. Chem. 15, 241-248. In brief, Saccharomyces cerevisiae, was transformed with the human estrogen receptor (ERα) gene, together with expression plasmids containing responsive elements and the lacZ reporter gene (encoding the enzyme β-galactosidase). β-galactosidase activity is quantified at 540 nm by the conversion of the chromogenic substance chlorophenol red-β-D-galactopyranoside into chlorophenol red. The bioassay response is expressed as the absorbance at 540 nm divided by the optical density at 630 nm [(A540/A630)$_{net}$]. The estrogenic activity of the samples was expressed as percentage equivalence to 10 nM estradiol (E2) which elicited a 100% response in the estrogen receptor bioassay. The bioassays were performed in 96-well plates in which 10 µL of the test compounds were tested and incubated with 240 µL of the genetically modified yeast (optical density of 0.25 at 610 nm). Serial dilutions of the test compounds were made in dimethylsulfoxide, which allowed generating dose-response curves for doses (ordinate) versus activity (abscissa). The data were fitted by a 4 parametric logistic model using the Marquardt-Levenberg algorithm (Sigmaplot 4.0, SPSS Inc., Chicago, Ill., USA) (De Boever et al. (2001) Env. Health Perspectives 109, 691-697).

The results are provided in FIG. 3. None of the incubations showed an estrogenic response at day 0. After 8 days, a strong increase in the estrogenic properties was seen in culture C (FIG. 3), but not in cultures A, B or D (data not shown). These results indicate the capacity of fecal culture C to convert IX in compounds with increased estrogenic properties. To further test this transformation, cultures A-D (10% (v/v)) were incubated for 8 days in Brain Heart Infusion broth (with 0.5 g/l cystein-HCl) with either X or IX at a concentration of 25 mg/l under anaerobic conditions and conversion products were detected by HPLC (Table 1). IX proved to be recalcitrant to transformation in cultures A, B and D which is in accordance with the results from the Yeast Estrogenic Screen. However, in culture C almost 40% of 8-PN was recovered, which explains the increase in estrogenic properties of culture C. X was slightly converted to IX in all samples but, as this was also detected when X was incubated with autoclaved cultures, this was a non-enzymatic isomerisation. In culture C, again a small amount of 8-PN was detected which was originated from the conversion of IX by human fecal bacteria.

TABLE 1

Microbial transformation of X and IX after incubation with fecal samples A, B, C and D.

| Substrate | % Recovery* | | | % Recovery | | |
|---|---|---|---|---|---|---|
| | X | IX | 8-PN | X | IX | 8-PN |
| | Sample A | | | Sample B | | |
| X | 74.9 (10.7) | 5.9 (0.8) | n.d. | 80.5 (2.5) | 9.1 (2.4) | n.d. |
| IX | n.d. | 90.1 (6.3) | n.d. | n.d. | 83.0 (5.1) | n.d. |
| | Sample C | | | Sample D | | |
| X | 73.6 (3.1) | 2.2 (0.1) | 5.3 (0.2) | 65.4 (4.2) | 11.7 (1.6) | n.d. |
| IX | n.d. | 19.0 (2.9) | 36.4 (7.4) | n.d. | 86.0 (4.5) | n.d. |

*results are presented as average (stdev) molar percentage recovery of X, IX or 8-PN relative to the dosed amount of flavonoid.
$^a$n.d.: below detection level The present results show the capacity of intestinal bacteria to transform X and IX into 8-PN through the process of enzymatic O-demethylation of the methoxy-group on the 5-position of the components. But not all cultures were able to perform this reaction. Therefore, the remaining cultures E-L (10% (v/v)) were incubated for 3 days in Brain Heart Infusion broth (with 0.5 g/l cystein-HCl) under anaerobic conditions with 25 mg/l IX (FIG. 4). The microbial O-demethylation of IX was only detected in samples E, J and K.

The present example shows that methylated prenylflavonoids are not metabolically inert after ingestion but can be activated into biologically (more) active demethylated derivatives. However, this transformation capacity strongly depends on the composition and activity of the intestinal microbial community, as the activation of IX occurred in only a third of the tested samples.

To further investigate these inter-individual differences, a total of 51 fecal samples were incubated for 3 days in Brain Heart Infusion broth (with 0.5 g/l cystein-HCl) under anaerobic conditions, containing 25 mg/l IX (FIG. 5). The results are presented as % 8-PN production relative to the incubated IX concentration and samples were ordered by increasing 8-PN production capacity. The data were analyzed by Two Step Cluster analysis and 3 groups were retrieved (designated a, b and c), with significantly different means (P<0.01, Kruskal-Wallis).

These data show that the activation of methylated prenylflavonoids is dependent on the intestinal microbial community, separating individuals into high (group c, 16%), moderate (group b, 22%) and slow (group a, 63%) 8-PN producers. In general the final exposure to the active component will depend rather on a combination of precursor concentration and the transformation potential of the intestinal microbial community.

Example 2

Use of Microorganisms to Produce Compounds with Estrogenic Properties of the Type 8-Prenylnaringenin The present example describes the capacity of two well-characterized intestinal anaerobic bacteria of converting IX into 8-PN.

*Eubacterium limosum* ATCC 8486 and *Peptostreptococcus productus* ATCC 27340 were obtained from the German Collection of Microorganisms and Cell Cultures (DSMZ, Braunschweig, Germany). *E. limosum* was incubated for 13 days in Brain Heart Infusion broth (with 0.5 g/l cystein-HCl) with 25 mg/l of IX and 8-PN under anaerobic conditions (Table 2). This strain was able to convert IX into 8-PN. The strain did not further degrade 8-PN, as all 8-PN, when give as a substrate could be recovered after 13 days of incubation. This feature is clearly different from the metabolic pathway as observed in liver microsomes wherein 8-PN is extensively further metabolised [Nikolic et al. (2005) *J. of Mass Spectrom.* 40, 289-299; Nikolic et al. (2004) *Drug Metabolism and Disposition* 32, 272-279].

TABLE 2

Transformation of IX and 8-PN by *E. limosum*.

| substrate | Eubacterium limosum % Recovery* | | | |
|---|---|---|---|---|
| | X | IX | 8-PN | 6-PN |
| IX | n.d. | 51.4 (4.6) | 36.4 (11.6) | n.d. |
| 8-PN | n.d. | n.d. | 98.3 (1.0) | 0.4 (0.1) |

*results are presented as average (stdev) molar percentage recovery of X, IX, 8-PN or 6-PN.
ⁿn.d.: not detected Because of the capacity of *E. limosum* to transform IX into 8-PN, a selection procedure was performed to obtain a strain, capable to quantitatively produce 8-PN. The selection procedure consisted of 6 parallel incubations of *E. limosum* [cultures from single colonies] with 25 mg/l IX and incubation for 8 days. Next, the culture which produced the highest amount of 8-PN was selected and used as inoculum for the next round of 6 parallel incubations (Table 3). While in the first selection round the lowest production was only 2%, an increase of up to 82% was apparent after three selection steps and the most efficient culture transformed all the dosed IX into 8-PN. The mean production of all six incubations in each round increased from 22.5% up to 90.5% and the standard deviation decreased from 20% to 7% after the selection procedure. This means that, after only three rounds, a strain was selected which converted almost all IX (high mean) and was also stable (low standard deviation).

TABLE 3

Selection of 8-PN producing *E. limosum* by 3 repeated incubations.

| | Molar % IX ⇒ 8-PN conversion | | |
|---|---|---|---|
| Selection round | I | II | III |
| Lowest | 2.1 | 24.3 | 82.1 |
| Highest | 46.5 | 79.4 | 102.5 |
| Mean (stdev) | 22.5 (19.3) | 57.9 (19.6) | 90.5 (6.9) |

To test the capacity of *P. productus* to perform the enzymatic conversion from IX into 8-PN, the strain was incubated in triplicate for 13 days in Brain Heart Infusion broth (with 0.5 g/l cystein-HCl) with 25 mg/l of IX under anaerobic conditions. Samples were analyzed every 2 days and the concentrations of IX and 8-PN were determined (FIG. 6). Depending on the incubation, *P. productus* transformed 10% to 50% of the incubated IX into 8-PN. This shows that this strain is also suitable for the production of 8-PN. *P. productus* strains can be further selected for enhanced demethylation activity, following the rationale, as described for *E. limosum*.

A specific example of a bacterial strain which has been enriched *Eubacterium limosum* has been deposited with the Belgian Coordinated collections of Microorganisms (BCCM) in the BCCM/LMG collection with deposit number LMG P-23546 on March 15$^{th}$, by Willy Verstraete

Example 3

Use of Microorganisms to Convert Methylated Prenylflavonoids in a Fermentation Setting A fed batch fermentation experiment was designed to use a selected strain *Eubacterium limosum* as obtained above, to convert methylated prenylflavonoids in a fermentation setting. Fermentation was performed in a Braun Biostat® M fermentor (2 l vessel), filled with 1.5 L Brain Heart Infusion broth (with 0.5 g/l cystein-HCl). Subsequently, the fermentor was sterilized by autoclaving it for 30 min at 121° C. Before inoculation, the fermentor was made anaerobic by flushing the system for 1 h with nitrogen gas. After this, the fermentor was inoculated with a 2-days old *E. limosum* culture and 25 mg/L IX was added to the fermentation liquid. The fermentation was performed at 37° C. for 2 weeks, without pH control. From day 1 on, three times/day 200 ml anaerobic Brain Heart Infusion broth (with 0.5 g/l cystein-HCl), containing 25 mg/L IX was dosed to the reactor at 10 ml/min and simultaneously 200 ml/min fermentor content was removed from the system. A 10 ml sample was taken from the effluent, for chemical analysis. This was done at day 0, 1, 2 and afterwards every 2 days. Data were as % conversion (8-PN/(IX+8-PN)). A conversion of 0% (day 0), 43% (day 1) and 100% (day 2 and following days), of IX into 8-PN was obtained.

This example shows that the selected strain was able to convert IX into the highly estrogenic 8-PN in a fermentation based strategy, leading to applications such as the production of products with estrogenic properties from precursors, with the aim to purify the compound of interest for use as ingredient for other applications or to activate the precursor in hop extracts or other vegetable extracts comprising methylated prenylflavonoids.

Example 4

Strain Supplementation Initiates Ex Vivo Conversion of IX into 8-PN

The most efficient *E. limosum* strain, obtained from the selection experiment in example 2, was supplemented to the originally non-converting culture B of example 1, to examine the capacity of this strain to initiate the production of 8-PN in the complex environment of a fecal suspension. The strain was added to the culture in proportions ranging from 0% up to 100% (v/v). This mixture was incubated with 10% (v/v) of 25 mg/L IX for a period of seven days in Brain Heart Infusion broth (with 0.5 g/l cystein-HCl) under anaerobic conditions. The concentration of 8-PN was monitored every two days (FIG. 7). The results show that, with increasing supplementation of *E. limosum*, the production of 8-PN increased. An equal amount of *E. limosum* culture and fecal sample (100% in FIG. 7) gave a complete conversion of IX into 8-PN, but even at 1% supplementation, half of the dosed IX was already transformed into 8-PN after only one day. Remarkably, a maximum concentration of 8-PN was reached for all incubations at the first day, which indicates that all the available IX was immediately transformed. No further conversion of 8-PN was detected as the concentration of 8-PN at day one and seven were not significantly different (Student T-test, $p > 0.05$).

This example shows that the selected strain was able to convert IX into the highly estrogenic 8-PN in the complex environment of a fecal culture, leading to possible applications, such as in situ conversion of precursors into products with estrogenic properties, in other diverse media such as hop extracts or other vegetable extracts comprising methylated prenylflavonoids.

Example 5

Conversion of Methylated Prenylflavonoids in a Dynamic In Vitro Simulation Model of the Intestinal Tract In a next step, to demonstrate the in situ conversion of precursors such as IX into products with estrogenic properties such as 8-PN, a dynamic in vitro simulation model of the intestinal tract was used (Simulator of the Human Intestinal Microbial Ecosystem (SHIME)), (Molly et al. (1993) *Appl. Microbiol. Biotechnol.* 39, 254-258). The SHIME consists of a succession of five reactors that represent the different parts of the human gastrointestinal tract. The first two reactors (stomach [reactor 1] and small intestine [reactor 2]) are of the fill-and-draw principle to simulate different steps in food uptake and digestion, with peristaltic pumps adding a defined amount of SHIME feed (3 times/day) and pancreatic and bile liquid to the stomach and duodenum compartment and emptying the respective reactors after specified intervals. The last three compartments (resp. ascending [reactor 3], transverse [reactor 4] and descending colon [reactor 5]) are continuously stirred reactors with constant volume and pH control. Retention time and pH of the different vessels were chosen in order to resemble in vivo conditions in the different parts of the gastrointestinal tract. The passage of food in the small intestine was simulated in reactor 2 by the addition of 60 ml artificial pancreatic and bile liquid, pancreatin and $NaHCO_3$. The temperature of the system was kept at 37° C. by a thermostat and the system was kept anaerobic by flushing it with $N_2$ for 15 min every day. Inoculum was prepared from faecal matter as described in De Boever et al. (2000) *J. Nutrition* 130, 2599-2606. Reactor 3, 4, and 5 were filled with nutritional medium and pH was adjusted to the respective pH range. Finally, 50 ml inoculum was added to the last three reactors.

For the present experiment, two of the above described systems were combined as two completely separate reactors, which are driven by the same pumps (pumps with two pump heads, allowing to dose exactly the same amounts of liquids to both systems), have identical pH and temperature control and which receive the same liquid food. This way, all parameters are perfectly controlled and identical, except for the intestinal microbial communities in the 2 systems which can be introduced separately. In this case we introduced a community which was capable to activate methylated prenylflavonoids (PF+) and one which could not (PF−). After a two-week stabilization period in which normal SHIME feed was dosed, 25 mg/L IX was dosed to the SHIME feed for 4 weeks (day 15-44). In the last two weeks the selected *Eubacterium limosum* strain of example 2, was also administered to the first colon compartment, to simulate the application of the strain as a probiotic (day 30-44).

FIGS. 7 and 8 show concentrations of IX and 8-PN in the ascending, transverse and descending colon parts for PF+ and PF− communities. In the PF+ compartment, activation of methoxylated prenylflavonoids was noted in the distal colon parts when only IX was administered (day 15-30), whereas no conversion occurred in the PF− compartment. After supplementing the bacterial strain (from day 30), the activation potential increased in the PF+ compartment and also in the PF− compartment, and production of the estrogenically active 8-PN was detected in the distal colon part.

This example shows that the selected strain of example 2 was able to activate methylated prenylflavonoids under simulated conditions of the human intestine.

Example 6

Demonstration of the In Vivo 5-Alkoxy Prenylflavonoid Demethylation Capacity of the Selected Strain of Example 2

An experiment with axenic and Human Flora Associated (HFA) rats was performed to test the capacity of the selected strain of example 2 to activate methylated prenylflavonoids in vivo. A total of 12 axenic rats were used for the study. When the rats were 5 weeks old, 3 HFA rats were associated by oral gavage with a freshly voided, homogenized fecal culture which has prenylflavonoid demethylating activity. These HFA rats were designated PF+ rats.

At the same time, 3 HFA rats were associated by oral gavage with a freshly voided, homogenized fecal culture without prenylflavonoid demethylating activity. These HFA rats were designated PF− rats. The remaining rats were kept under sterile conditions. All rats were kept in separate, closed collective cages prior to the start of the experiment.

After 3 weeks of stabilization of the microbial cultures inside the rat intestine, a first experiment was started. After moving the rats to individual metabolism cages, 2 mg IX/kg body weight was daily administered to each rat for 5 days and each day 24 h-pooled urine was collected. After 3 days, the urinary IX and 8-PN excretion was quantified. The conversion [8-PN/(IX+8-PN)] is presented in Table 4. Hereafter, the rats were transferred back to the collective cages for 2 weeks prior to the second part of the experiment.

Herein, the 6 axenic rats were associated with the selected *E. limosum* strain of example 2 for 7 days by daily oral gavage with a log 9 bacterial suspension. On day 2, the rats were transferred to the individual metabolism cages for 24 h-pooled urine collection. From day 2 until day 7, 2 mg IX/kg BW was administered to the rats by oral gavage. On day 7, the urinary IX and 8-PN excretion was quantified. The conversion [8-PN/(IX+8-PN)] is presented in Table 4.

TABLE 4

Mean and Stdev 24 h-pooled urinary % 8-PN/(IX + 8-PN) excretion.

|  | IX<br>Mean (Stdev) | IX + *E. limosum*<br>Mean (Stdev) |
|---|---|---|
| PF+ | 55.3 (9.1) | |
| PF− | 23.6 (10.4) | |
| Axenic | 0.0 (0.0) | 41.1 (16.8) |

This example shows that the activation of methylated prenylflavonoids is a solely microbial phenomenon, as axenic rats did not produce 8-PN. Moreover, differences in the intestinal transformation capacity lead to a different 8-PN excretion as the urine of the PF+ rats had a higher 8-PN ratio, compared to the PF− rats. Finally, this example indicates that the selected *E. limosum* strain can activate methylated prenylflavonoids in vivo, as the axenic rats started to produce 8-PN after being associated with this bacterium.

The invention claimed is:

1. A method for producing 8-prenylnaringenin in vitro said method comprising the steps of:
    a) providing a first composition comprising an effective amount a bacterial strain selected from the group consisting of *Eubacterium limosum* LMG P-23546, *Eubacterium limosum* ATCC 8486, and *Peptostreptococcus productus* ATCC 27340,
    b) contacting a second composition comprising isoxanthohumol with said first composition so as to allow dealkylation of said isoxanthohumol by said bacterial strain, and
    c) recovering 8-prenylnaringenin produced.

2. The method according to claim 1, which further comprises enriching the dealkylating activity of said bacterial strain by repeated incubations with desmethylxanthohumol.

* * * * *